United States Patent
Tkachuk (10) Patent No.: US 7,570,360 B1
(45) Date of Patent: Aug. 4, 2009

(54) OPTICAL ABSORPTION SPECTROMETER AND METHOD FOR MEASURING CONCENTRATION OF A SUBSTANCE

(75) Inventor: Michael Tkachuk, St. Petersburg (RU)

(73) Assignee: Bah Holdings, LLC, Glen Cove, NY (US)

( * ) Notice: Subject to any disclaimer, the term of this patent is extended or adjusted under 35 U.S.C. 154(b) by 0 days.

(21) Appl. No.: 11/670,280

(22) Filed: Feb. 1, 2007

(51) Int. Cl.
*G01N 21/00* (2006.01)

(52) U.S. Cl. .................. 356/437; 250/339.07; 702/189

(58) Field of Classification Search .................. 356/437, 356/246, 301, 335, 454, 327; 250/339.07; 702/189
See application file for complete search history.

(56) References Cited

U.S. PATENT DOCUMENTS

| | | | |
|---|---|---|---|
| 4,736,103 A * | 4/1988 | Nelson et al. | 250/343 |
| 4,885,469 A | 12/1989 | Yamagishi et al. | |
| 5,696,586 A | 12/1997 | Ivanov | |
| 6,147,351 A * | 11/2000 | Huiku | 250/343 |
| 6,956,648 B2 * | 10/2005 | Loicht et al. | 356/323 |
| 7,063,667 B1 * | 6/2006 | Ben-Oren et al. | 600/532 |
| 2003/0090670 A1 * | 5/2003 | Capetanopoulos | 356/453 |

FOREIGN PATENT DOCUMENTS

| | | |
|---|---|---|
| EP | 0 359 213 | 3/1990 |
| EP | 0 396 319 | 11/1990 |
| WO | WO 01/65219 A1 | 6/2001 |
| WO | WO 01/40748 A1 | 9/2001 |

OTHER PUBLICATIONS

Search report mailed Jul. 27, 2001 for PCT Application PCT/GB01/00711.
Search report mailed May 3, 2001 for PCT Application PCT/GB00/04523.

* cited by examiner

*Primary Examiner*—Tarifur Chowdhury
*Assistant Examiner*—Michael Lapage
(74) *Attorney, Agent, or Firm*—James P. Muraff; Neal, Gerber & Eisenberg LLP (57) ABSTRACT

An optical absorption spectrometer is provided for determining the concentration of a substance within a sample. The optical absorption spectrometer comprises a first radiation source for supplying radiation to the sample to be measured; at least one cavity for containing the sample during measurement; and a detector assembly for detecting radiation transmitted along first and second optical paths through the sample, the length of the first optical path being greater than that of the second optical path.

21 Claims, 10 Drawing Sheets

OPTICAL ABSORPTION SPECTROMETER AND METHOD FOR MEASURING CONCENTRATION OF A SUBSTANCE

TECHNICAL FIELD

The present invention relates to an optical absorption spectrometer for determining the concentration of a substance within a sample, and in particular for the optical detection of gases.

BACKGROUND OF THE INVENTION

A number of optical gas detection techniques exist and are based on the measurement of the absorption of incident radiation by the gas molecules. For example, non-dispersive infrared (NDIR) spectroscopy involves using a detector to monitor radiation transmitted by a sample when exposed to a radiation source. By measuring the radiation absorbed by the sample within a particular wavelength range, the concentration of a target gas in the sample can be determined.

As explained in WO-A-01/65219 and WO-A-01/40748, another known type of optical absorption gas detector is the correlated interference polarisation spectrometer (CIPS). A CIPS works on the principle that for any given wavelength incident radiation, the quantity that is absorbed by the gas is a function of the cross-section ($\sigma(\lambda)$) of any particular molecule of the gas. If the dependence of the cross-section on the wavelength is very pronounced, then the gas molecules will absorb radiation over a very narrow waveband. Accordingly, the spectral displacement between the maximum and minimum intensities of the transmitted radiation is very small. By measuring the difference between the maximum and minimum intensities of the transmitted radiation, it is possible to calculate the concentration of the gas.

Figure 1:
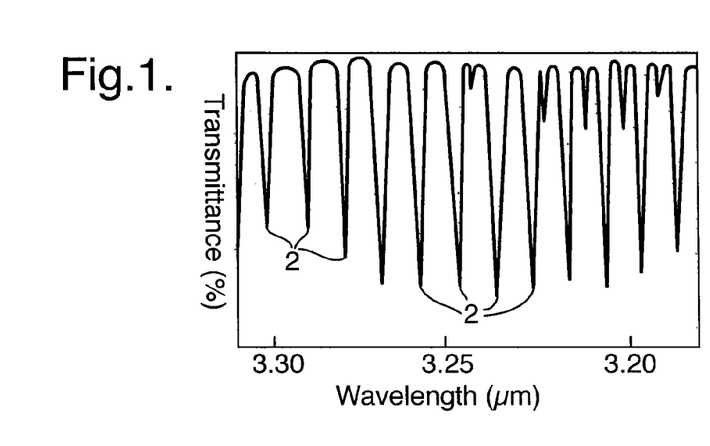
FIG. 1 is a graph showing the absorption spectrum of methane around 3.25 microns.

The CIPS uses the quasi-periodical structure of the electronic absorption spectrum of the gas molecules, which occurs due to their vibrational-rotational properties. FIG. 1 shows, as an example, the absorption spectrum of methane in the vicinity of 3.25 micrometers. The spectrum consists of a number of very narrow (approximately 1 nm wide) quasi-periodic absorption bands, labelled 2, that are detected by the CIPS.

In order to detect the quasi-periodic structure, the CIPS filters radiation transmitted by the sample gas using a comb filter which is generated by a controlled interference polarisation filter (cIPF). The cIPF is formed from a modified interference polarisation filter (IPF) which uses the phenomenon of birefringence in certain crystals to obtain a transmission spectrum which is characterised by a quasi-periodic sequence of spectral passbands.

In order to be able to use the IPF in the detection of gases, the IPF must provide a transmission spectrum that closely matches the quasi-periodic absorption spectra of the gas to be detected (i.e. the bandwidth between adjacent peaks in the absorption spectrum of the gas to be detected must correspond to the bandwidth between adjacent transmission peaks in the IPF transmission spectrum). Furthermore, the IPF must be able to shift this spectrum in time so that one can detect the intensity of the radiation transmitted at both the absorption and non-absorption bands of the absorption spectrum of the target gas. Various ways of achieving this are disclosed in WO-A-01/65219.

It will be appreciated that, whilst this description will generally refer to the detection of gases, the techniques and apparatus disclosed herein could be used for the measurement of any substance.

One problem frequently encountered in many types of optical absorption spectrometer, including NDIR devices and CIPS apparatus, is that the measurement range of the instrument is inherently limited. For example, a CIPS of the sort described in WO-A-01/65219 and WO-A-01/4702 has a measurement range typically limited to three or four orders of magnitude. For concentrations below its desired range, the CIPS does not have the sensitivity (i.e. signal/noise ratio) to measure the concentration accurately. For concentrations above its designed range, the signal output by the CIPS saturates and will not respond properly.

One factor which contributes to this problem is the design of the cavity used to contain the gas sample during test. For high sensitivity, a long gas cavity having for example an optical path between 20 cm and 30 cm is required in order to ensure that there is a sufficient number of gas molecules in the chamber to achieve detectable absorption at low gas concentration levels and obtain a reasonable signal in the presence of noise. The disadvantage of using a long optical path is that, in the presence of higher gas concentrations, substantially all the radiation is absorbed by the gas molecules before it can reach the detector (in accordance with Beer's law). As such, it is not presently possible to use a single apparatus for the accurate measurement of high gas concentrations as well as low gas concentrations.

The problem is also made worse by the dependence of the measured radiation signal on uncontrollable measurement conditions. For example, factors such as dust occurring in the optical system or radiation beam misalignment, etc., can decrease the incident radiation intensity, leading to an erroneous concentration measurement.

What is needed is an optical absorption spectrometer which can operate across a wide range of target gas concentrations. It would also be advantageous is the measurement signal were less effected by changes in the lighting conditions.

SUMMARY OF INVENTION

In accordance with a first aspect of the invention, an optical absorption spectrometer for determining the concentration of a substance within a sample comprises a first radiation source for supplying radiation to the sample to be measured;

at least one cavity for containing the sample during measurement; and a detector assembly for detecting radiation transmitted along first and second optical paths through the sample, the length of the first optical path being greater than that of the second optical path.

The first aspect of the invention further provides a method of determining the concentration of the substance within the sample, comprising transmitting radiation through the sample to be measured along a first optical path and a second optical path, the length of the first optical path being greater than that of the second optical path;

filtering the radiation transmitted through the sample using a filter having a number of pass bands at wavelengths corresponding to absorption peaks in the absorption spectrum of the substance to be detected, the filter being responsive to an applied signal to modulate the wavelengths of the pass bands; and detecting the filtered radiation to determine the difference in its maximum and minimum intensities to thereby determine the concentration of the substance in the sample.

The provision of first and second optical paths in this way enables the spectrometer to be used for accurate measurement of both low and high gas concentrations. At low gas concentrations, the longer optical path provides high sensitivity, whereas at high concentrations the shorter optical path contains relatively few gas molecules such that a measurement can still be taken. The signal received by the detector assembly is effectively a superposition of the radiation received along each optical path. There may of course be any number of different optical paths through the sample, provided there are at least two.

In a preferred embodiment, the dimension of the at least one cavity coaxial with the first optical path is greater than the dimension of the at least one cavity coaxial with the second optical path. That is, it is the dimensions of the cavity itself which are used to provide at least two alternative optical paths through the sample of differing lengths. Conveniently, the first and second optical paths are parallel to one another, although this need not be the case.

Where the first and second optical paths are parallel, it is preferred that the dimension of the cavity parallel to the first and second optical paths varies in a direction perpendicular to the axes of the first and second optical paths. In this way, manufacture and control of the cavity dimensions is simplified since the profile of the cavity need only vary across one of its faces.

The variation of the cavity dimension could take any form, e.g. curved, but preferably, in a first example, the dimension of the cavity parallel to the first and second optical paths varies in a stepwise manner. In other cases, it is preferable for the dimension of the cavity parallel to the first and second optical paths to vary continuously, preferably linearly.

Variation of the cavity dimensions can be achieved in numerous ways. In one particularly preferred embodiment, the cavity is defined within a chamber, the chamber comprising cavity varying means for varying the cavity dimensions. In most cases, the cavity dimensions are varied spatially, but could be varied temporally as an alternative or in addition.

Advantageously, the cavity varying means comprise at least one chamber wall for dividing the cavity from a sample-free volume. In this way, the cavity can be readily defined with an appropriate dimension profile and the sample excluded from the remainder of the chamber. Preferably, the sample-free volume contains a radiation transparent material, preferably nitrogen. Solid materials such as transparent polymers are convenient alternatives.

In other examples, the cavity varying means advantageously comprise chamber walls for defining the cavity therewithin, the chamber walls varying in their thickness. This conveniently provides a single "gas cell" component having a regular external shape, if desired, yet a internal cavity of varying dimension. In the locality of the optical paths, the chamber walls are preferably radiation transparent.

In an alternative embodiment, the cavity is advantageously provided with a first radiation guiding assembly for guiding radiation along the first optical path, and a second radiation guiding assembly for guiding radiation along the second optical path.

In this way, a cavity of regular dimension can be employed and adapted to provide the first and second optical paths by appropriate arrangement of the guiding assemblies, which may comprise components defining at least part of the cavity walls.

Conveniently, the first and second guiding assemblies comprise a plurality of reflective elements, preferably mirrors or prisms (and which may form part of the cavity walls). In some examples, it is preferable that the first and second guiding assemblies further comprise one or more beam splitters for dividing radiation between the first and second optical paths.

In addition, it may be advantageous if the cavity dimensions themselves are adjustable such that the length of the first and/or second optical paths can be adjusted. This allows the spectrometer to be tuned according to the gas concentration range encountered.

In some embodiments, it is preferred that the optical absorption spectrometer further comprises a second radiation source for supplying radiation to the sample to be measured, the first radiation source being arranged to supply radiation along the first optical path, and the second radiation source being arranged to supply radiation along the second optical path.

It may further be advantageous if the detector assembly comprises first and second detector elements for detecting radiation transmitted through the sample, the first detector element being arranged to detect radiation on the first optical path, and the second detector element being arranged to detect radiation on the second optical path.

Either of these arrangements increases the number of configurations, and therefore different path lengths achievable, using the apparatus.

Preferably, the detector assembly further comprises a processor adapted to generate a measurement of the concentration of the substance in a sample from a radiation signal output by the detector. Advantageous processing techniques which could be used are discussed below.

In a particularly preferred embodiment, the optical absorption spectrometer is adapted for the detection of methane. It is especially preferred that the optical absorption spectrometer is a correlated interference polarization spectrometer and further comprises:

a filter for filtering radiation transmitted by the sample, the filter having a number of pass bands at wavelengths corresponding to absorption peaks in the absorption spectrum of the substance to be detected, the filter being responsive to an applied signal to modulate the wavelengths of the pass bands; wherein the detector assembly comprises a processor for determining the difference in the minimum and maximum intensities of the detected radiation to thereby determine the concentration of the substance in the sample.

In accordance with a second aspect of the invention, a detector assembly for use in an optical absorption spectrometer for determining the concentration of the substance within a sample comprises:

a radiation detector for detecting radiation transmitted by the sample to be measured and generating a signal in accordance with the detected radiation; and a processing circuit coupled to the radiation detector and comprising averaging means adapted to generate a first signal representing the average intensity of the detected radiation, $L_{AV}$, and comparison means adapted to generate a second signal representing the relative intensities of the maxima and minima of the detected radiation, $L_{CIPS}$, wherein the processing circuit is adapted to generate a normalised output signal, $S_{NORM}$, based on a ratio of the second signal to the first signal, to thereby determine the concentration of the substance.

By outputting a normalised signal in this way, it has been found that the concentration range across which the assembly can generate accurate measurements is increased. Moreover, the dependence of the concentration signal on incident radiation intensity is reduced. In particular, unintentional reductions in radiation intensity for reasons such as dust in the system and radiation beam misalignment will not affect the normalised value.

Nonetheless, for long radiation paths, the normalised signal still suffers as a result of increased radiation absorption (particularly at higher concentrations), and it has therefore been found advantageous if the processing circuit is further adapted to generate an average output signal, $S_{AV}$, corresponding to the first signal, $L_{AV}$, to thereby determine the concentration of the substance.

The average output signal $S_{AV}$, represents the total intensity of radiation transmitted through the sample. Where the radiation is infrared, this corresponds to NDIR detection. Therefore, the average output signal $S_{AV}$ provides a second way of calculating the concentration of the substance in the sample. Whilst the normalised CIPS output signal, $S_{NORM}$, gives accurate results at low concentrations, it has been found that this average output signal $S_{AV}$ provides good measurement results at higher concentrations.

Therefore, in a particularly preferred embodiment, the processing circuit is adapted to generate the normalised output signal $S_{NORM}$ when the concentration of the substance is below a predetermined threshold, and to generate the average output signal $S_{AV}$ when the concentration of the substance is above the predetermined threshold.

In effect, the assembly can operate as a CIPS below the threshold and as an NDIR unit (or similar) above the threshold. Thus a broad concentration range can be measured.

Preferably, the predetermined threshold is defined as a proportion of the maximum $L_{CIPS}$ signal, preferably 70% of the maximum $L_{CIPS}$ signal. In other cases, the threshold could simply be defined as a set concentration level. For example, using the example of methane, the predetermined threshold may be 5% concentration by volume.

Advantageously the optical absorption spectrometer comprises a filter for filtering radiation transmitted by the sample, the filter having a number of pass bands at wavelengths corresponding to absorption peaks in the absorption spectrum of the substance to be detected, the filter being responsive to an applied signal to modulate the wavelengths of the pass bands, and the comparison means of the processing circuit is responsive to the applied signal to generate the second signal, $L_{CIPS}$.

Preferably, the comparison means comprises a lock-in amplifier referenced to the applied signal. Advantageously, the comparison means further comprises a bandpass filter.

This aspect of the invention further provides a correlated interference polarisation spectrometer for determining the concentration of a substance within a sample, the spectrometer comprising:

a radiation source for supplying radiation to the sample to be measured;

a filter for filtering radiation transmitted by the sample, the filter having a number of pass bands at wavelengths corresponding to absorption peaks in the absorption spectrum of the substance to be detected, the filter being responsive to an applied signal to modulate the wavelengths of the pass bands; and a detector assembly comprising a radiation detector for detecting the filtered radiation and generating a signal in accordance with the detected radiation, and a processing circuit coupled to the radiation detector, comprising averaging means adapted to generate a first signal representing the average intensity of the detected radiation, $L_{AV}$, and comparison means adapted to generate a second signal representing the relative intensities of the maxima and minima of the detected radiation, $L_{CIPS}$, the processing circuit generating a norma-lised output signal, $S_{NORM}$, based on a ratio of the second signal to the first signal, to thereby determine the concentration of the substance.

Preferably, the sample to be measured is contained within a cavity, at least one radiation path passing through the cavity. It is further advantageous to provide first and second radiation paths as specified by the first aspect of the invention in order to further broaden the concentration range of the instrument.

Preferably, the at least one radiation path is 30 cm or less in length, preferably 20 cm or less.

This aspect of the invention further provides a method of determining the concentration of a substance within a sample, comprising:

transmitting radiation through the sample to be measured;

filtering the radiation transmitted through the sample using a filter having a number of pass bands at wavelengths corresponding to absorption peaks in the absorption spectrum of the substance to be detected, the filter being responsive to an applied signal to modulate the wavelengths of the pass bands;

detecting the filtered radiation;

processing the detected radiation to generate a first signal representing the average intensity of the detected radiation, $L_{AV}$, and a second signal representing the relative intensities of the maxima and minima of the detected radiation, $L_{CIPS}$; and generating a normalised output signal, $S_{NORM}$, based on a ratio of the second signal to the first signal, to thereby determine the concentration of the substance.

BRIEF DESCRIPTION OF THE DRAWINGS

Examples of optical absorption spectrometers and methods for measuring the concentration of a substance within a sample in accordance with the present invention will now be described and contrasted with conventional systems with reference to the accompanying drawings, in which:—

DETAILED DESCRIPTION OF THE PREFERRED EMBODIMENTS

Figure 2:
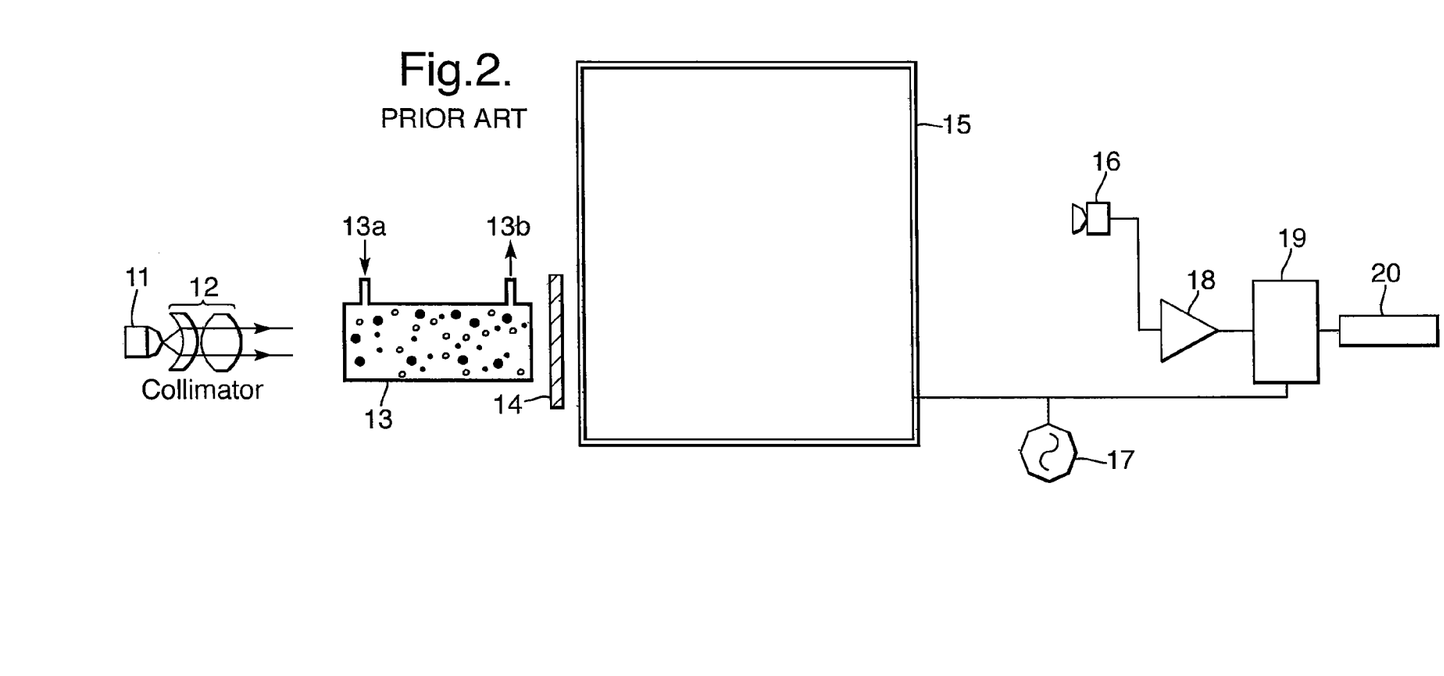
FIG. 2 is a schematic diagram of an example of a known CIPS apparatus.

An example of a conventional CIPS adapted to detect the quasi-periodic structure of the gas molecules' absorption spectrum is shown in FIG. 2.

This type of spectrometer can be operated either as an active device using an emitter, such as an incandescent lamp, or as a passive device, using the sun as an emitter. The design shown in FIG. 2 is for an active CIPS system.

The CIPS includes a radiation source 11 such as an LED, a laser or the like positioned next to a collimator 12. The collimator 12 operates to convert the incident radiation into a collinear beam which then passes through a cavity 13. The cavity 13 contains the gas to be detected and includes an input aperture 13A and an output aperture 13B. Radiation transmitted through the cavity 13 is then filtered using a narrow band filter 14 which allows only wavelengths in the vicinity of the desired absorption spectra to pass. Thus for example to detect methane then the bandpass filter would allow radiation in the 3.25 micrometer region to pass.

Following the filter 14 is a controlled interference polarisation filter (cIPF) section 15. The cIPF 15 generates a transmission spectrum that consists of very narrow pass bands coinciding with the quasi-periodic absorption spectrum of the target gas. The cIPF 15 is controlled to cause the transmission spectrum to be scanned back and forth within the selected working range. The operation of the cIPF 15 is controlled by an alternating voltage supply 17 which guides the cIPF and the detection system. The detection system consists of a detector 16 coupled to an amplifier 18 which operates to amplify a signal detected by the detector 16. The output of the amplifier 18 is coupled to a microprocessor 19 and is also coupled to the alternating voltage supply 17 so as to synchronise the processing of the detected signal with the operation of the cIPF 15. The signals obtained from the microprocessor 19 are then output to a display 20 which displays an indication of the concentration of the detected gas.

Any form of IPF such as a SOLC or Lyot filter can be used. However, it is preferred to use either a Woods filter including input and output polarisers and an etalon formed from a birefringent crystal, as described in WO-A-01/40748, or a photoelastic modulator of polarisation (PMP) as described in WO-A-01/65219.

As explained in the aforementioned publications, the transmission spectrum of the cIPF 15 includes a number of transmission peaks such that it acts as a comb filter. By appropriate choice of components, the transmission peaks can be selected to correspond to absorption peaks in the vibrational-rotational spectrum of the target gas. Accordingly, with the transmission and absorption peaks aligned, the radiation transmitted by the cIPF 15 will be the radiation having wavelengths which are absorbed by the target gas. The state of the cIPF can then be changed, for example by applying a stress, causing its transmission spectrum to alter. Accordingly, the comb filter effectively scans from left to right and then back again across the wavelength spectrum.

When the transmission peaks are aligned with troughs in the vibrational-rotational spectrum then the radiation transmitted by the cIPF 15 represents wavelengths which are transmitted by the target gas. This allows the maximum and minimum transmission intensities in the absorption spectra of the gas to be determined (i.e. the height of the peaks can be determined). Thus by choosing an appropriate amplitude driving signal, the cIPF 15 can act as a modulator, scanning the vibrational-rotational spectrum of the sample gas from one maxima to the next and back again.

To measure the concentration of gas, the microprocessor 19 is adapted to determine the intensity of radiation received at the detector 16 at the time when the peaks of the cIPF transmission spectrum are aligned with the maxima of the vibrational-rotational spectrum of the target gas, and then at the time when the peaks of the cIPF transmitter spectrum are aligned with the troughs of the target gas spectrum. By correlating this information with an indication of the relative transmission intensities of the cIPF, this allows the microprocessor 19 to determine the relative intensities and the spectral displacement of the peaks and troughs in the vibration or rotational spectrum. This in turn allows identification of the target gas, and the measurement of its concentration, to be achieved.

However, as already described, in common with other types of optical absorption spectrometers, CIPS of the type shown in FIG. 2 suffer from the limitation that they can only take concentration measurements over a narrow range of concentrations, typically limited to three or four orders of magnitude. For high sensitivity measurements, the design of the spectrometer requires a long gas cavity 13 having typically an optical path of between 20 and 30 cm, potentially through the use of multi-pass chambers. It is necessary to increase the absolute number of absorbing molecules in order to get sufficient absorption at very low gas concentration levels to obtain a reasonable signal in the presence of noise.

The disadvantage of using a long optical path through the sample cavity 13 is that in the presence of higher gas concentrations, essentially all of the radiation is absorbed by the gas molecules. This reduces the flexibility of the system to simultaneously detect both very low gas concentrations and high gas concentrations.

Figure 3:
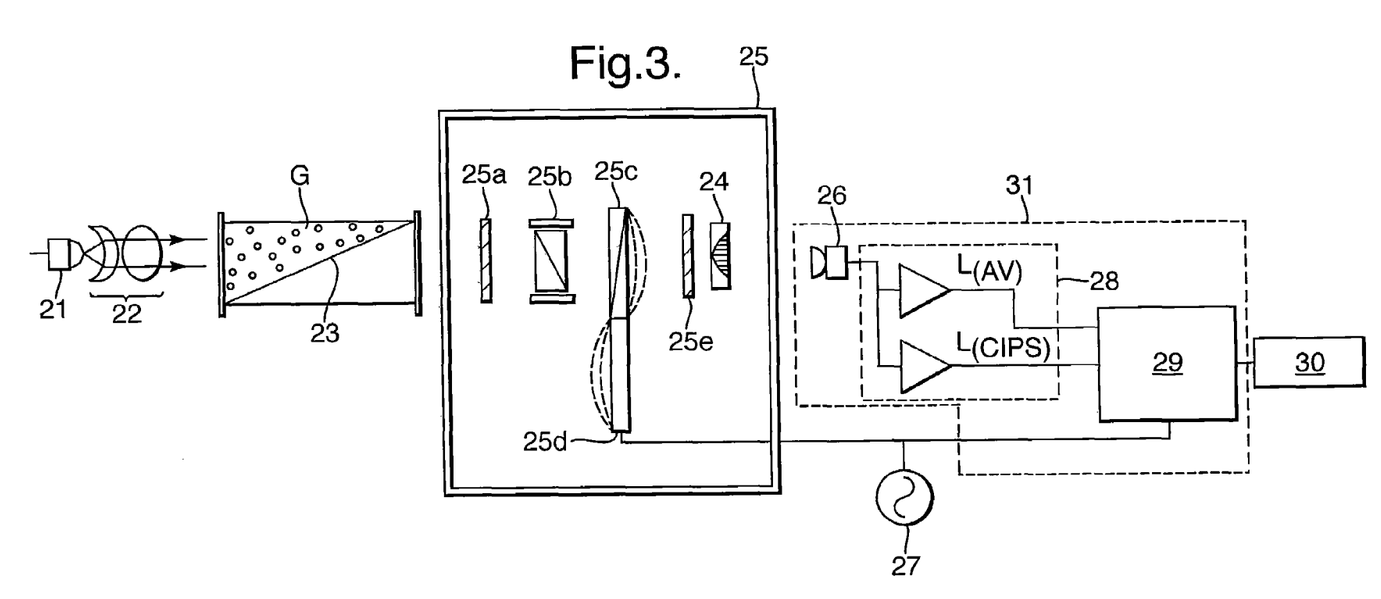
FIG. 3 is a schematic diagram of a CIPS apparatus in accordance with a first embodiment of the invention.

FIG. 3 shows a first embodiment of the present invention, which is a CIPS having a modified gas cavity 23. The remaining components shown in FIG. 3 largely correspond to the FIG. 2 example.

A radiation source 21 such as a lamp, LED or laser, generates a radiation beam which is collimated by collimator 22 to pass through cavity 23 containing gas G which is the sample to be measured. Radiation transmitted by the gas G passes to the controlled interference polarization filter (cIPF) section 25. Here, the cIPF is shown to comprise two polariser elements 25a and 25e either side of an etalon 25b and a crystal 25c which exhibits induced birefringence. The birefringence is induced by a piezoelectric driver 25d supplied from an AC voltage 27 and synchronised with the processor 29.

In this example, the last component of cIPF 25 is a bandpass filter 24 which corresponds in function to filter 14 shown in FIG. 2.

Radiation transmitted by the cIPF 25 is detected by detector assembly 31 which comprises a photodetector 26, amplifying means 28 and processor 29. In this example, the amplifying means 28 is shown to produce two outputs as will be described in further detail below. However, a single amplifier such as component 18 shown in FIG. 2 could be used instead. As in the prior art system, processor 29 can be adapted to detect the difference in intensities between the peaks and troughs and thereby generate a concentration measurement which is output on display 30.

Gas cavity 23 differs from prior art systems in that, due to its shape, radiation passing through the cavity at one position will traverse a path through the gas sample G which differs in length to that traversed by radiation passing through the cavity 23 at a different position. In particular, in the example of FIG. 3, the cavity 23 has a triangular cross-section which is arranged such that, in the direction of radiation propagation, the dimension of the cavity is greater towards its upper surface (as shown in the diagram) than at its lower extremity. A first exemplary optical path through the cavity adjacent its top surface therefore has a greater length than a second exemplary optical path passing through the cavity close to its lower extremity. The longer path provides for high sensitivity measurements, and the short path provides for measurement at high concentrations. The radiation received by the detector 26 via the cIPF 25 is essentially a superposition of Beer's law for more than one path.

Figure 4:
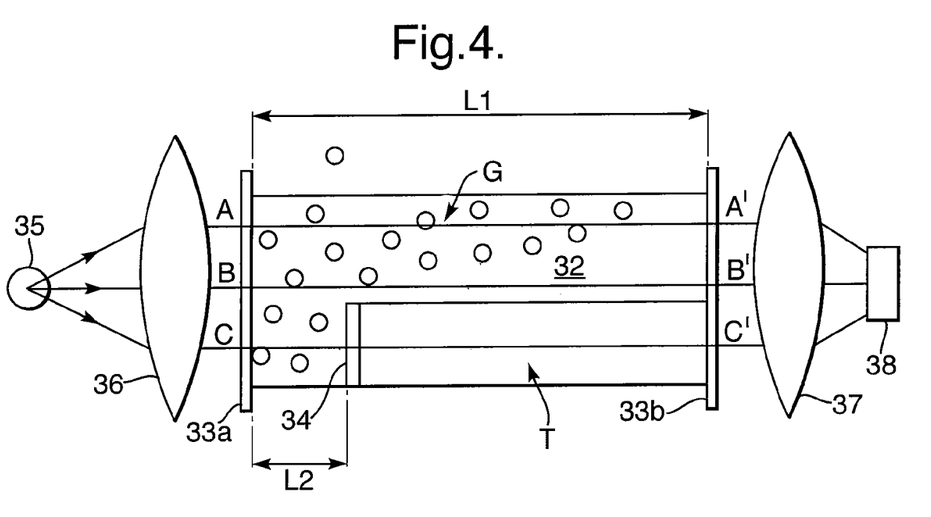
FIG. 4 shows a schematic diagram of a sample cavity arrangement for use in an optical absorption spectrometer in accordance with a second embodiment of the invention.

A simpler example of a suitable gas cavity used in a second embodiment of the invention is shown in FIG. 4. Here, the cavity 32 is defined between walls 33a and 33b of a chamber which comprises means for varying the cavity dimensions in the form of a partition 34 dividing off a volume containing radiation-transparent material T. The walls 33a and 33b and the partition 34 are all substantially transparent to the radiation, at least in the vicinity of the radiation beam(s) passing therethrough. The radiation transparent material T may be a solid material (e.g. it could be a continuation of the wall 33B or the partition 34), or it could be an inert gas such as nitrogen, i.e. one which does not absorb the radiation. The presence of volume T effectively causes the cavity dimension parallel to the radiation beam to vary along a perpendicular direction in a stepwise manner.

For clarity, FIG. 4 does not show the surrounding components of the spectrometer (which could be a CIPS or NDIR spectrometer, for example), and instead simply illustrates a radiation source 35 and detector 38 together with lenses 36 and 37 which provide a collimated radiation beam through the sample gas G and directly transmits radiation on to detector 38.

Three exemplary radiation rays, AA', BB', and CC' are illustrated. The uppermost rays, AA' and BB' pass through the upper portion of the cavity 32 whereas the lower radiation ray CC' passes through the lower portion of the cavity 32 as well as the partition 34 and the radiation transparent material T. The dimension of the cavity 32 coaxial with radiation ray AA' is greater than the dimension of the cavity coaxial with the radiation ray CC'. Thus the radiation on path AA' may be said to follow an optical path through the sample G which is longer than that on a second optical path CC'. Radiation on the first optical path AA' traverses a distance $L_1$ through the gas sample whereas radiation on the optical path CC' traverses a distance $L_2$ through the gas sample before it reaches the partition 34 and is then passed to the detector 38 without encountering any further gas molecules.

The radiation detected by the photodetector 38 is the sum of the radiation received along each path. The long path AA' provides for high sensitivity and can measure low gas concentrations since sufficient gas molecules are present along the path to cause enough absorption to be detected. The short path CC', on the other hand, provides for the detection of high gas concentrations since the relatively small number of molecules which can be accommodated across the distance $L_2$ means that some radiation still arrives at the detector 38.

The radiation detected by the photodetector 38 is a superposition of Beer's law for each path. Taking the two paths AA' and CC', the detected radiation is:

$$I=I_1\exp(-aCL_1)+I_2\exp(-aCL_2)$$

where a is an extinction coefficient, C is the concentration of the gas and $I_1$ and $I_2$ are the intensities of the radiation passing along optical paths $L_1$ and $L_2$ respectively. Since $L_1$ is greater than $L_2$, at low gas concentrations the first term is dominant, whereas at high gas concentrations, the second term dominates the resultant radiation.

In another example, the cavity of FIG. 4 could be used without the partitioned volume T, eg by providing two radiation sources and two detectors, and arranging the two optical paths to pass through the cavity in perpendicular directions, one crossing the long dimension of the cavity and the other the short.

Figure 5:
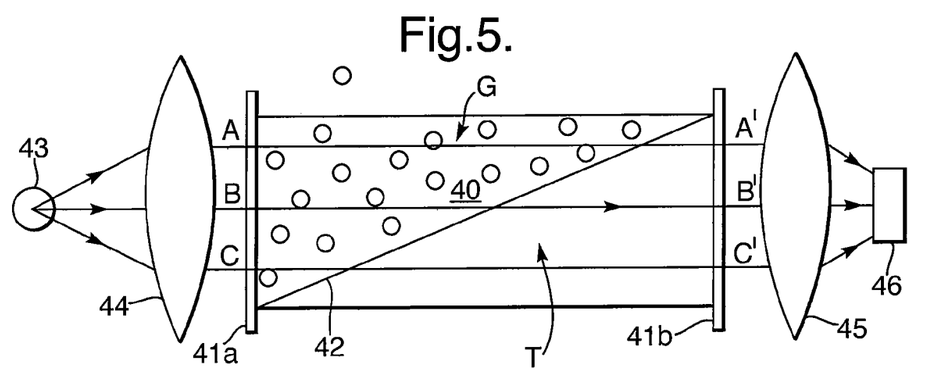
FIG. 5 shows a second sample cavity arrangement for use with an optical absorption spectrometer according to a third embodiment of the invention.

FIG. 5 shows another cavity for use in a third embodiment of an absorption spectrometer. As in the embodiment of FIG. 3, here the cavity 40 has a triangular cross-section.

The cavity 40 is defined within a chamber having walls 41a and b and a partition 42 creating a sample-free volume of radiation transparent material T. As in the example of FIG. 4, any radiation transparent material could be used, but nitrogen is particularly preferred. The partition 40 could be fixed or could be movable by a user such that the dimensions of the cavity 40 could be adjusted according to the measurement conditions.

As in FIG. 4, the three radiation rays AA', BB' and CC' are depicted. In this example, each of the paths traverses a different distance through the sample gas G since the dimension of the gas cavity 40 varies continuously from top to bottom. In this case, the variation is linear whereas in other cases any other function e.g. curved, sinusoidal or parabolic could be used instead.

Again, this arrangement allows for the sensitive detection of low gas concentrations via the longer optical paths AA' and BB', and for detection of high gas concentrations via the shorter optical path CC'. The radiation detected by the photodetector 46 can be approximated by the superposition of Beer's Law for each of the three paths:

$$I=I_1\exp(-aCL_1)+I_2\exp(-aCL_2)+I_3\exp(-aCL_3)$$

where a is an extinction coefficient, C is the concentration of the gas, and $I_1$ to $I_3$ are the intensities of radiation on optical paths AA', BB', and CC' through the sample having optical path lengths of $L_1$ to $L_3$ respectively.

In practice, there are of course an infinite number of light paths AA', BB' etc passing though the cavity, which make up the radiation beam. The cavity dimension changes continuously across the beam's cross section. Hence, the total radiation detected by the photodetector 46 can be more accurately represented by:

$$I=\Sigma_i I_i\exp(-aCL_i)$$

where $I_i$ is the intensity of the light on optical path i, having a path length $L_i$ through the cavity, and a and C are as previously defined. The optical paths i are defined between the two outermost paths, AA' and CC'.

Figure 6:
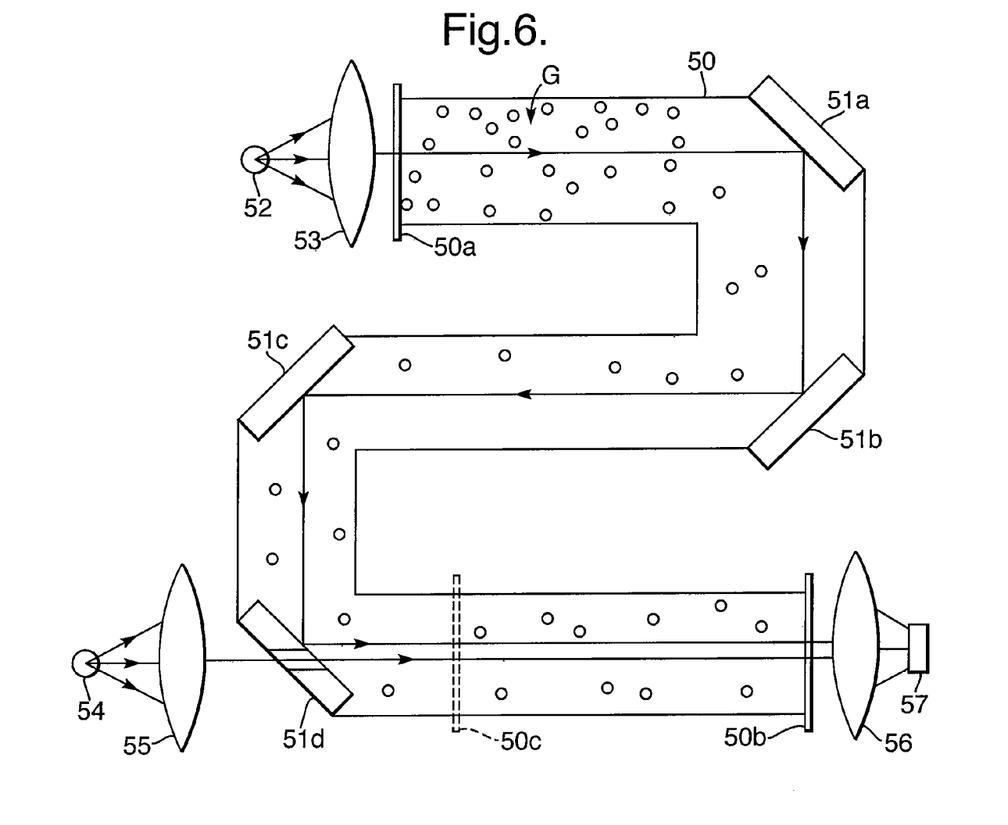
FIG. 6 shows a third sample cavity arrangement for use with a optical absorption spectrometer in accordance with a fourth embodiment of the invention.

FIG. 6 shows a fourth embodiment of a cavity 50 containing the gas sample G. In this case, the cavity 50 itself follows a convoluted path between radiation-transparent end plates 50a and 50b. At each corner, a reflective element 51a to 51d is provided to guide radiation along the cavity. The reflective elements could comprise mirrors or prisms, and could be integral with the walls of the cavity 50.

A first radiation source 52 is provided adjacent the first end 50A of the cavity 50. Radiation from the source 52 passes through a collimating lens 53 into the cavity 50 where it is guided along the convoluted length of the cavity 50 by reflective elements 51a to *d* toward end plate 50b where radiation is focussed by lens 56 onto detector 57. This constitutes a first optical path through the gas sample G.

A second, shorter optical path is configured by providing a transparent window in reflective element 51d through which radiation from a second radiation source 54, collimated by lens 55, enters the gas cavity 50. Having entered the gas cavity 50 a significant distance after the radiation from the first radiation source 52, radiation on the second optical path has a relatively short distance to travel before exiting the cavity via plate 50b onto detector 57.

Optionally, the cavity dimensions can be made adjustable in which case end plate 50b may be movable along the axis of the cavity to change the length of the two optical paths. This is particularly useful for very high concentration gas measurements since the second optical path can be made very short. Reference numeral 50c in FIG. 6 denotes the end plate moved to a position in which the optical paths are shortened.

As in the previous embodiments, here the detected radiation is a sum of that received from each optical path. It will be noted that the embodiment of FIG. 6 differs from the first three embodiments in that, in the main, the different optical path lengths are achieved not by varying dimensions of the cavity but by arranging for radiation to be guided along two separate paths through the cavity. In this way, reflective elements 51a to *d* can be thought of as constituting a first radiation guiding assembly for passing radiation along the first optical path, and the transparent mirror 51d alone as constituting a second radiation guiding assembly passing radiation along the second optical patch through the cavity 50.

Figure 7:
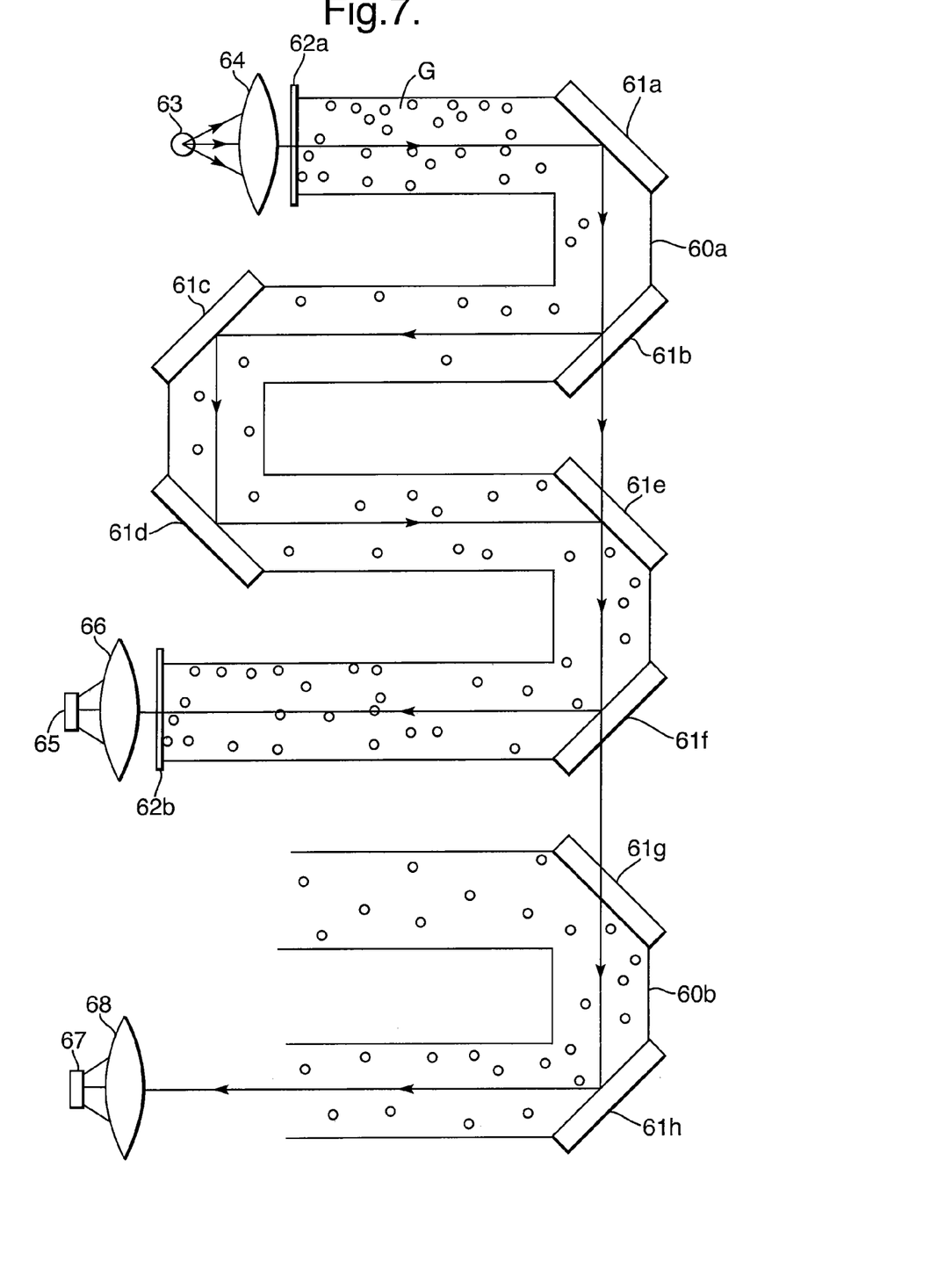
FIG. 7 shows a fourth sample cavity arrangement for use with a optical absorption spectrometer in accordance with a fifth embodiment of the design.

FIG. 7 illustrates a fifth embodiment which works on similar principles. Here, the gas cavity 60 comprises a main section 60a and, optionally, an extension section 60b. Like the FIG. 6 embodiment, the cavity 60a follows a convoluted path. The radiation entering the cavity from radiation source 63 via collimator lens 64 and cavity end wall 62a is directed around the corners of the cavity by reflective elements 61a to *f*. Radiation reflected along the entire length of the cavity 60a follows the longest path before exiting the cavity via end wall 62b and focusing lens 66 on to detector 65. The reflective elements 61a to *f* make up a first radiation guiding assembly.

To provide a second, shorter, optical path through cavity 60a, reflective elements 61b and 61e are half-silvered or provided with a transparent window. Thus, when the radiation reaches reflective element 61b, the beam is split such that one portion follows the first optical path whereas a second portion passes through the reflective element 61b and re-enters the cavity through reflective element 61e. The beam then rejoins the first optical path and is reflected by element 61f into detector 65. The second radiation guiding assembly comprises elements 61a, 61b, 61e and 61f. Thus, this second optical path is shorter than the first by virtue of cutting out the central "bend" of the cavity. These two optical paths can be used to detect high and low gas concentrations as previously described.

In some cases, it may be advantageous to include one or more further optical paths for higher accuracy. This could be achieved by making more elements of the radiation guiding arrangement semi-transparent, for example element 61c, so that radiation can exit at different points along the cavity. Alternatively, an extension cavity 60b can be provided which receives radiation from one such semi-transparent element, 61f, passes it through a further sample of gas (using additional reflective elements 61g and 61h) before reaching a second detector 67 through focussing lens 68. The output from detectors 65 and 67 can be used in conjunction to determine the total radiation transmitted by the sample as a whole. The cavities 60A and 60B may or may not be in direct fluid communication with one another.

By knowledge of the distance each optical path travels within the cavity 60a and, where used, 60b, similar equations to those mentioned above can be used to deduce the gas concentration.

Figure 8:
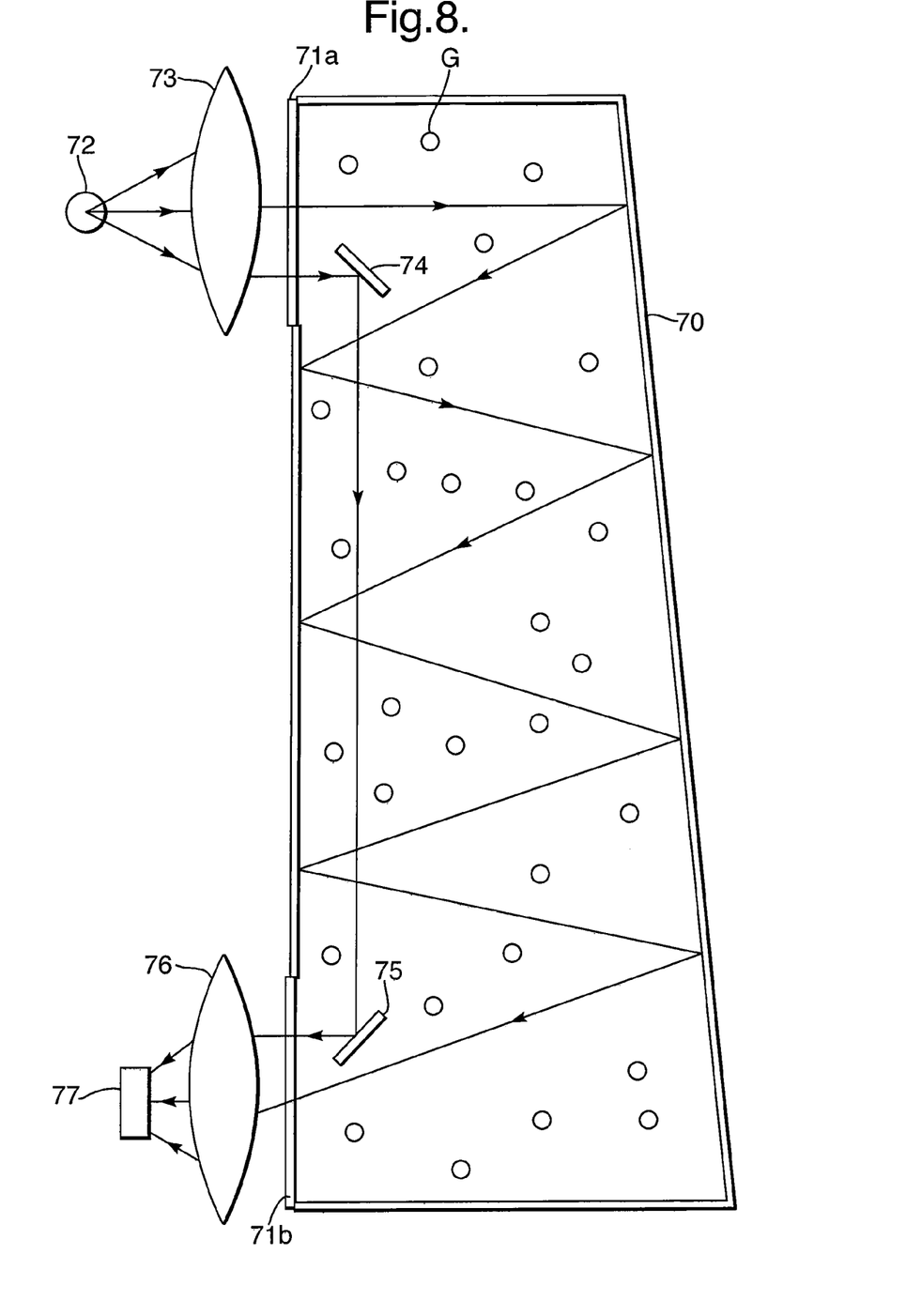
FIG. 8 shows a fifth sample cavity arrangement for use with an optical absorption spectrometer in accordance with a sixth embodiment of the invention.

FIG. 8 shows a sixth embodiment which uses a cavity 70 having a comparatively regular shape. The cavity 70 is defined by end plates 71a and 71b together with walls having an at least partially reflective internal surface. Radiation from a source 72 passes via a collimator lens 73 into the cavity 70 through first end plate 71a. Radiation is reflected off each internal wall of the cavity, undergoing multiple passes of the cavity's width, until it reaches end plate 71b where it exits the cavity via focussing lens 76 to detector 77. This constitutes a first optical path through the cavity 70, and the internal reflective walls constitute a first radiation guiding arrangement.

To establish a second radiation path through the cavity 70, reflective elements 74 and 75 are disposed within the cavity 70 adjacent to the first end wall 71a and second end wall 71b respectively. Reflective element 74 diverts a portion of the radiation received from source 72 such that it bypasses the internal walls of the cavity 70 and strikes reflective element 75 which guides the radiation directly out of the cavity through wall 71b and toward detector 77. This second optical path in the cavity is therefore significantly shorter than the first. Reflective elements 74 and 75 make up the second radiation guiding assembly.

As before, the radiation detected at detector 77 is the sum transmitted along each of the optical paths.

Each of the above embodiments can be used in otherwise conventional optical absorption spectrometers such as the CIPS shown in FIG. 2 or in NDIR systems. In a CIPS system, further advantages can be achieved by replacing the conventional detected signal algorithm with a detector assembly operating on the principle schematically illustrated in FIG. 9. It should be noted that this detector assembly can also be used in CIPS assemblies employing conventional gas cavities.

Figure 9:
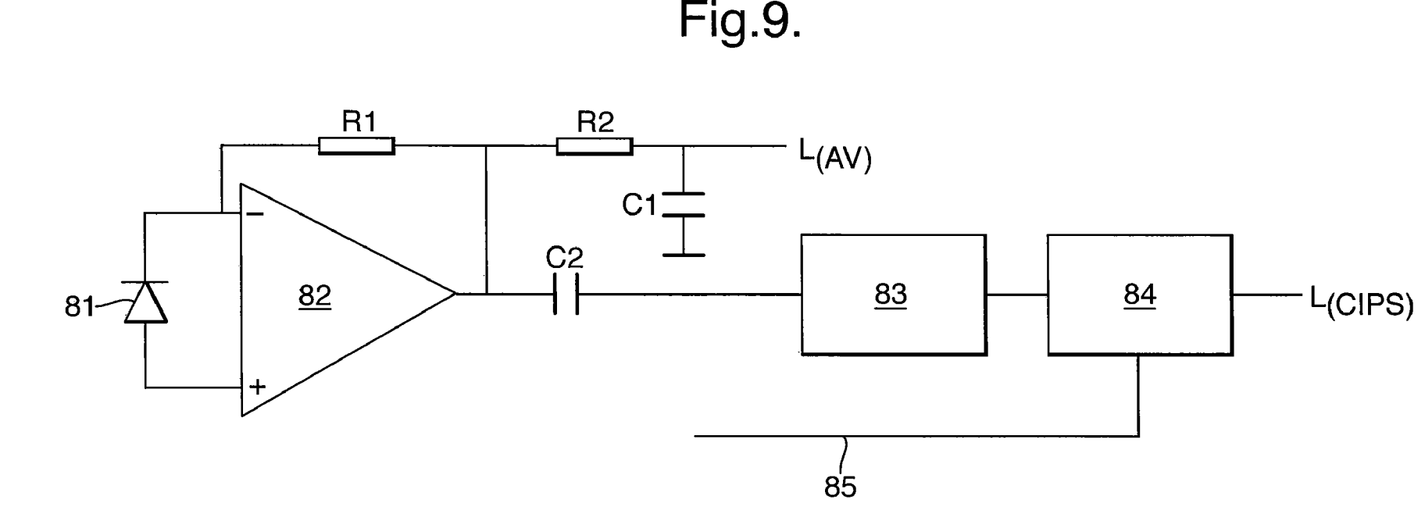
FIG. 9 shows a schematic circuit diagram forming part of a detector assembly in accordance with a seventh embodiment of the present invention.

In a CIPS, as described above, radiation transmitted by the moving comb filter is received by a detector 81 (FIG. 9). In conventional systems, this signal is amplified and synchronised to the modulator generator signal resulting in a sinusoidal output signal whose amplitude is related to the difference in intensity between the maximum and minimum of the vibrational-rotational gas spectrum. This signal is hereinafter referred to as "$L_{CIPS}$".

Figure 10:
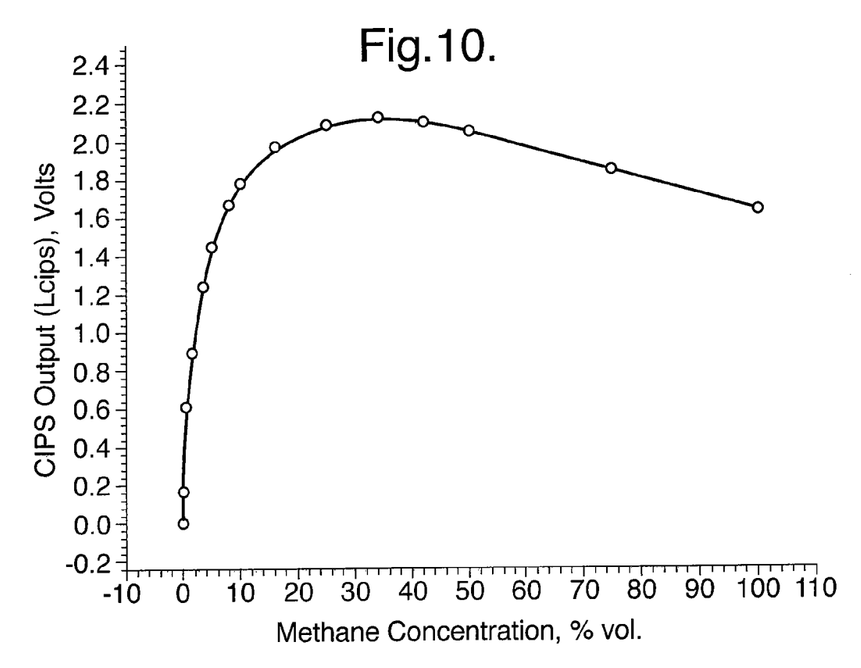
FIG. 10 is a graph showing the output of a CIPS and its dependency on concentration, using the example of methane.

FIG. 10 is a graph showing the typical response of a conventional $L_{CIPS}$ signal to changes in gas concentration (here using the example of methane as the substance under test). It will be seen that at low concentrations the difference between the absorption band and the transmission band signals increases with the concentration of the gas. For higher concentrations, the absorption band signal saturates and the difference is no longer increased. For still higher concentrations the overall transmission band signal begins to drop, making it difficult to produce an accurate measurement.

Figure 11:
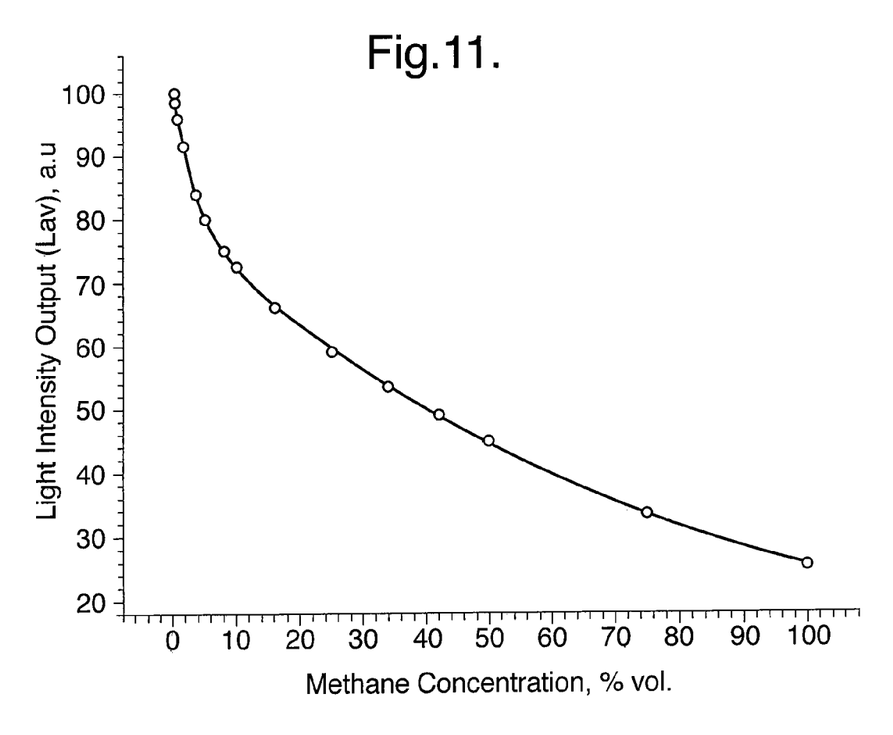
FIG. 11 is a graph showing the average radiation intensity signal and its dependence on methane concentration.

Using the detection assembly proposed according to a seventh embodiment of the invention, as shown in FIG. 9, in addition to generating the $L_{CIPS}$ signal (using band pass filter 83 and lock in amplifier 84 to synchronise with control signal 85), the average radiation intensity, $L_{AV}$, transmitted by the sample is also calculated. Radiation incident on detector 81 is amplified by amplifier 82 and split into two signals by an arrangement of resistors R1 and R2 and capacitors C1 and C2. The configuration of resistor R2 and the capacitor C1 constitutes an averaging circuit which averages the signal received from the comb filter over time. To achieve this, the components should meet the following condition:

$$R_2 C_1 \gg 1/2\pi f_0$$

where $f_0$ is the frequency of the CIPS signal modulation on line 85 (FIG. 9). The average radiation intensity signal $L_{AV}$ follows Beer's law. Its dependence on concentration is shown in FIG. 11, again using the example of methane.

Figure 12:
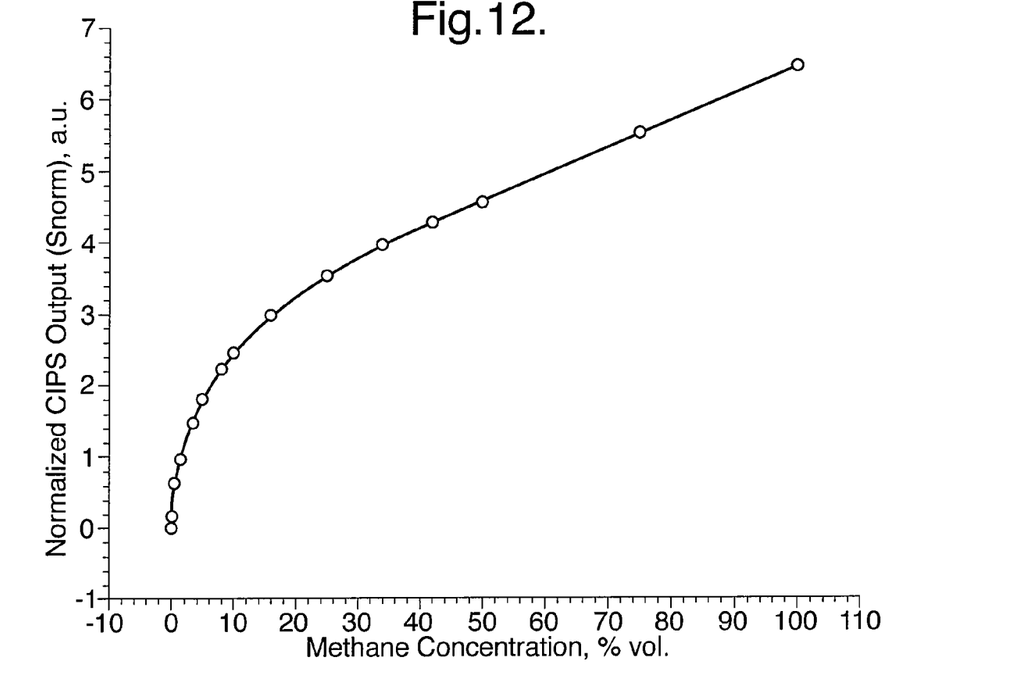
FIG. 12 is a graph showing the normalised output signal and its dependency on methane concentration.

By dividing the modulated CIPS signal $L_{CIPS}$ by the average photodetector output $L_{AV}$, the CIPS signal is normalised ("$S_{NORM}$"). This is depicted in FIG. 12. As is evident from FIG. 12, the normalised output signal $S_{NORM}$ demonstrates a good signal response verses concentration over a very wide range. Moreover, as well as improving the concentration range, the use of this normalised signal also reduces the dependence of the output on the intensity of incident radiation. For example, any changes in the output of the radiation source or residual factors such as dust in the optical system will not effect the value of the normalised signal.

Such detection techniques have been found to be particularly useful for optical absorption spectrometers with relatively short radiation paths no more than about 20 cm. In more sensitive analysers (1 ppm and better) with longer radiation paths (30 cm and more) the effects of absorption are still so significant that at high concentrations it is difficult to obtain an accurate measurement.

To address this, the detector assembly shown in FIG. 9 preferably provides two outputs: the normalised CIPS signal, $S_{NORM}$, and an average photodetector output $S_{AV}$ which is derived directly from the average photodetector signal $L_{AV}$ described above.

Figure 13:
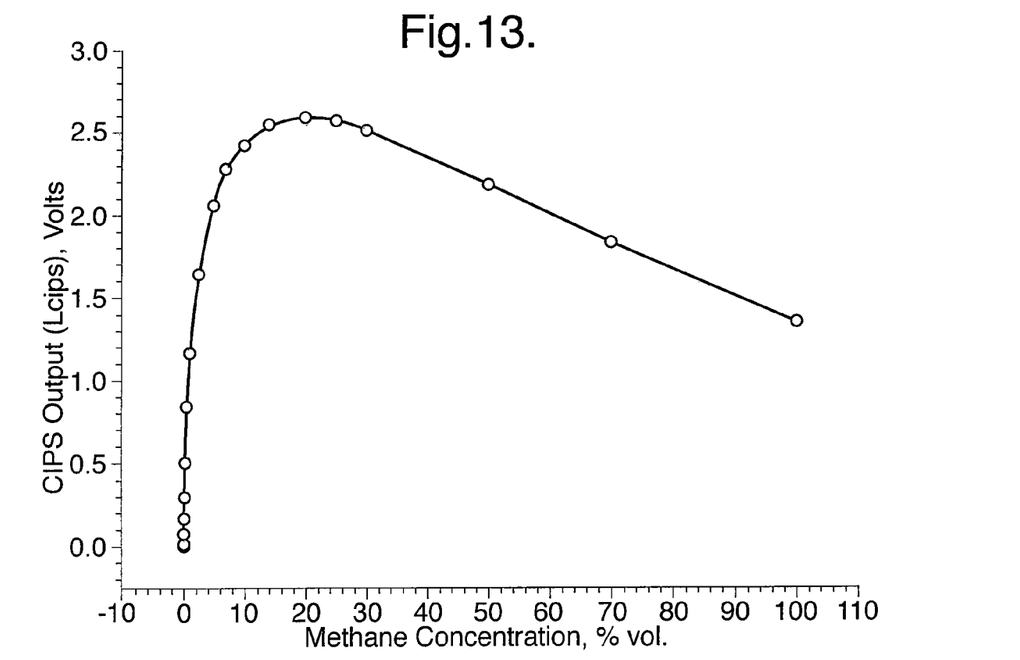
FIG. 13 is a graph showing the output of a CIPS having a longer optical path, and its dependency on methane concentration.
Figure 14:
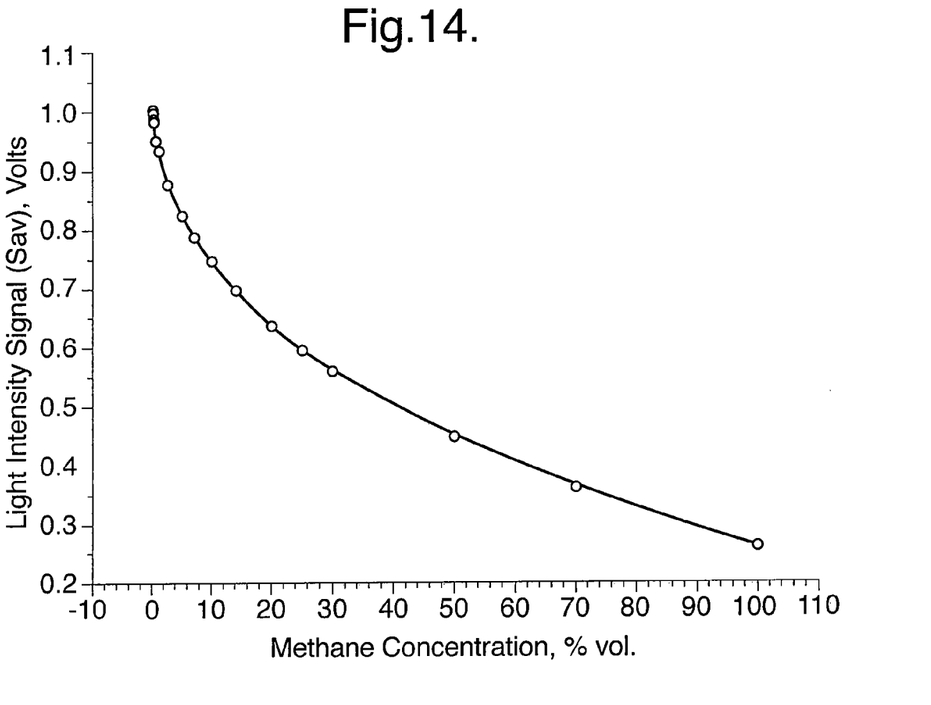
FIG. 14 is a graph showing the average radiation intensity signal of the same system; and, FIG. 15 is a graph showing the normalised output signal in the same system.

FIG. 13 shows the modulated photodetector output $L_{CIPS}$ signal for a conventional CIPS apparatus having a long optical path (35 cm in this example). It will be seen that the signal drops sharply for concentrations greater than approximately 20%. FIG. 14 shows the average photodetector output for the same CIPS apparatus. As before, this follows Beer's Law.

Figure 15:
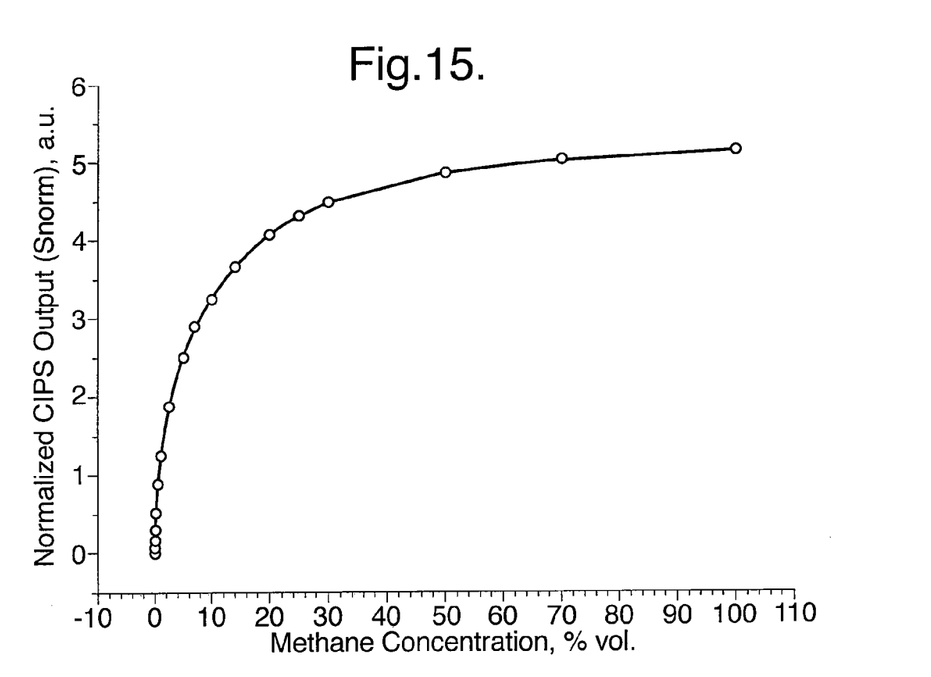

FIG. 15 shows the normalised photodetector output $S_{NORM}$ for the same apparatus having a 35 cm optical path. At gas concentrations higher than approximately 50%, it is clear that the signal becomes saturated and cannot be used for accurate measurements of such gas concentrations. However, the present inventors have recognised that the average photodetector output signal $S_{AV}$ shows significant concentration dependence in this region and can therefore be used to provide a measurement of gas concentration with reasonable accuracy (about 2%). The average photodetector output signal $S_{AV}$ corresponds to the signal which would be obtained using NDIR technology (assuming the apparatus utilises infra red radiation). Effectively, the CIPS apparatus can be used as an NDIR unit for the measurement of high gas concentrations.

It is therefore proposed to provide the detector assembly with additional processing for outputting the $S_{NORM}$ signal when the detected gas concentration is below a predetermined threshold, and output the average photodetector signal $S_{AV}$ when the detected gas concentration exceeds that threshold. It may also be advantageous to output both signals across an intermediate range of concentrations. For example, the processor may output the $S_{NORM}$ signal when the gas concentration is below a first threshold, then output both the $S_{NORM}$ and $S_{AV}$ signals between the first threshold and a second, higher threshold, and output only the $S_{AV}$ signal above the second threshold.

The value of the predetermined threshold can be selected according to the measurements being undertaken. Typically, taking methane as an example, the normalised CIPS output ($S_{NORM}$) is accurate in the approximate range 0 to 5% vol (100% lower explosion limit of methane), and the $S_{AV}$ output can be used for gas concentrations from 5% to 100% vol. Alternatively, the threshold value could be linked to a proportion of the maximum $L_{CIPS}$ signal. For example, referring to FIG. 13, if the predetermined threshold is defined as 70% of the maximum $L_{CIPS}$ signal (approximately 1.8V), this corresponds to a methane concentration of approximately 4% volume.

These detection algorithms can be used in combination with a conventional gas cavity, but gas cavities providing first and second optical paths, as described with reference to the first to sixth embodiments are preferred in order to obtain maximum benefits.

I claim:

1. A detector assembly for use in an optical absorption spectrometer for determining the concentration of a substance within a sample, the detector assembly comprising:
   a radiation detector for detecting radiation transmitted by the sample to be measured and generating a radiation signal in accordance with the detected radiation; and
   a processing circuit coupled to the radiation detector and comprising averaging means adapted to generate, from the radiation signal, a first signal representing the average intensity of the detected radiation, $L_{AV}$, and comparison means adapted to generate, from the radiation signal, a second signal representing the relative intensities of the spectral maxima and minima of the detected radiation, $L_{CIPS}$, wherein the processing circuit is adapted to generate a normalized output signal, $S_{NORM}$, based on a ratio of the second signal to the first signal, to thereby determine the concentration of the substance.

2. A detector assembly according to claim 1 wherein the processing circuit is further adapted to generate an average output signal, $S_{AV}$, corresponding to the first signal, $L_{AV}$, to thereby determine the concentration of the substance.

3. A detector assembly according to claim 2 wherein the processing circuit is adapted to generate the normalized output signal $S_{NORM}$ when the concentration of the substance is below a predetermined threshold concentration, and to generate the average output signal $S_{AV}$ when the concentration of the substance is above the predetermined threshold concentration.

4. A detector assembly according to claim 3 wherein the predetermined threshold concentration is defined as a proportion of the maximum $L_{CIPS}$ signal.

5. A detector assembly according to claim 4 wherein the predetermined threshold concentration is 70% of the maximum $L_{CIPS}$ signal.

6. A detector assembly according to claim 1 wherein the optical absorption spectrometer comprises a filter for filtering radiation transmitted by the sample, the filter having a number of pass bands at wavelengths corresponding to absorption peaks in the absorption spectrum of the substance to be detected, the filter being responsive to an applied signal to modulate the wavelengths of the pass bands, and the comparison means of the processing circuit is responsive to the applied signal to generate the second signal, $L_{CIPS}$.

7. A detector assembly according to claim 6, wherein the comparison means comprises a lock-in amplifier referenced to the applied signal.

8. A detector assembly according to claim 7 wherein the comparison means further comprise a band-pass filter.

9. A correlated interference polarization spectrometer for determining the concentration of a substance within a sample, the spectrometer comprising:

a radiation source for supplying radiation to the sample to be measured;

a filter for filtering radiation transmitted by the sample, the filter having a number of pass bands at wavelengths corresponding to absorption peaks in the absorption spectrum of the substance to be detected, the filter being responsive to an applied signal to modulate the wavelengths of the pass bands;

a detector assembly comprising a radiation detector for detecting the filtered radiation and generating a radiation signal in accordance with the detected radiation, and a processing circuit coupled to the radiation detector, comprising averaging means adapted to generate, from the radiation signal, a first signal representing the average intensity of the detected radiation, $L_{AV}$, and comparison means adapted to generate, from the radiation signal, a second signal representing the relative intensities of the spectral maxima and minima of the detected radiation, $L_{CIPS}$, the processing circuit generating a normalized output signal, $S_{NORM}$, based on a ratio of the second signal to the first signal, to thereby determine the concentration of the substance.

10. A correlated interference polarization spectrometer according to claim 9 wherein the processing circuit is further adapted to generate an average output signal, $S_{AV}$, corresponding to the first signal, $L_{AV}$, to thereby determine the concentration of the substance.

11. A correlated interference polarization spectrometer according to claim 10 wherein the processing circuit is adapted to generate the normalized output signal $S_{NORM}$ when the concentration of the substance is below a predetermined threshold concentration, and to generate the average output signal $S_{AV}$ when the concentration of the substance is above the predetermined threshold concentration.

12. A correlated interference polarization spectrometer according to claim 11 wherein the predetermined threshold concentration is defined as a proportion of the maximum $L_{CIPS}$ signal.

13. A correlated interference polarization spectrometer according to claim 12 wherein the predetermined threshold concentration is 70% of the maximum $L_{CIPS}$ signal.

14. A correlated interference polarization spectrometer according to claim 9 wherein the sample to be measured is contained within a cavity, at least one radiation path passing through the cavity.

15. A correlated interference polarization spectrometer according to claim 14 wherein the at least one radiation path is 30 cm or less in length.

16. A correlated interference polarization spectrometer according to claim 15 wherein the at least one radiation path is 20 cm or less in length.

17. A method of determining the concentration of a substance within a sample, comprising:

transmitting radiation through the sample to be measured;

filtering the radiation transmitted through the sample using a filter having a number of pass bands at wavelengths corresponding to absorption peaks in the absorption spectrum of the substance to be detected, the filter being responsive to an applied signal to modulate the wavelengths of the pass bands;

detecting the filtered radiation and generating a corresponding radiation signal;

processing the detected radiation signal to generate a first signal representing the average intensity of the detected radiation, $L_{AV}$, and a second signal representing the relative intensities of the spectral maxima and minima of the detected radiation, $L_{CIPS}$; and generating a normalized output signal, $S_{NORM}$, based on a ratio of the second signal to the first signal, to thereby determine the concentration of the substance.

18. A method according to claim 17, further comprising:

generating an average output signal, $S_{AV}$, corresponding to the first signal, $L_{AV}$, to thereby determine the concentration of the substance.

19. A method according to claim 18, wherein the normalized output signal $S_{NORM}$ is generated when the concentration of the substance is below a first predetermined threshold concentration, and the average output signal $S_{AV}$ is generated when the substance is above a second predetermined threshold concentration.

20. A method according to claim 19, wherein the first and second predetermined threshold concentrations are defined as a proportion of the maximum $L_{CIPS}$ signal.

21. A method according to claim 20, wherein the first and second predetermined threshold is concentrations are both 70% of the maximum $L_{CIPS}$ signal.

* * * * *